(12) United States Patent
Conklin

(10) Patent No.: US 12,004,945 B2
(45) Date of Patent: Jun. 11, 2024

(54) SURGICAL PROSTHETIC HEART VALVE

(71) Applicant: JVH of America, Irvine, CA (US)

(72) Inventor: Brian Scott Conklin, Orange, CA (US)

(73) Assignee: JILIN VENUS HAOYUE MEDTECH LIMITED, Jilin (CN)

( * ) Notice: Subject to any disclaimer, the term of this patent is extended or adjusted under 35 U.S.C. 154(b) by 79 days.

(21) Appl. No.: 17/395,266

(22) Filed: Aug. 5, 2021

(65) Prior Publication Data
US 2023/0042537 A1    Feb. 9, 2023

(51) Int. Cl.
*A61F 2/24* (2006.01)

(52) U.S. Cl.
CPC .......... *A61F 2/2409* (2013.01); *A61F 2/2418* (2013.01); *A61F 2230/0045* (2013.01); *A61F 2230/0054* (2013.01); *A61F 2230/0056* (2013.01); *A61F 2250/0018* (2013.01); *A61F 2250/0063* (2013.01)

(58) Field of Classification Search
CPC ............ A61F 2/2409; A61F 2230/0045; A61F 2230/0056; A61F 2/2445; A61F 2250/0063
See application file for complete search history.

(56) References Cited

U.S. PATENT DOCUMENTS

| | | | |
|---|---|---|---|
| 4,388,735 A | 6/1983 | Ionescu et al. | |
| 8,641,757 B2 | 2/2014 | Pintor et al. | |
| 9,364,322 B2 | 6/2016 | Conklin et al. | |
| 9,504,566 B2 | 11/2016 | Guttenberg et al. | |
| 9,554,901 B2 | 1/2017 | Cao et al. | |
| 9,848,984 B2 | 12/2017 | Conklin et al. | |
| 10,441,415 B2 | 10/2019 | Johnson et al. | |
| 10,456,246 B2 | 10/2019 | Conklin et al. | |
| 10,695,170 B2 | 6/2020 | Conklin et al. | |
| 10,751,174 B2 | 8/2020 | Conklin et al. | |
| 2006/0229718 A1* | 10/2006 | Marquez | A61F 2/2409 623/2.38 |
| 2007/0050021 A1* | 3/2007 | Johnson | A61F 2/2418 623/2.14 |
| 2011/0276128 A1* | 11/2011 | Cao | A61F 2/2412 623/2.11 |
| 2015/0289972 A1* | 10/2015 | Yang | A61F 2/2418 623/2.17 |
| 2017/0000603 A1* | 1/2017 | Conklin | A61F 2/2418 |

(Continued)

*Primary Examiner* — Matthew J Lawson
*Assistant Examiner* — Cassidy N Stuhlsatz
(74) *Attorney, Agent, or Firm* — Raymond Sun

(57) ABSTRACT

A surgical prosthetic heart valve has a supporting structure and a plurality of leaflets, the supporting structure generally having an annular shape with a blood flow channel defined in the annular shape and having opposite inflow and outflow sides along an axial direction of the annular shape, the plurality of leaflets connected to the supporting structure to control the blood flow channel to open or close. The supporting structure includes a first annular band and a second annular band, both of which are provided with deformable sections spaced from each other in the circumferential direction for allowing diameter expansion of the respective annular bands. The surgical heart valve achieves the diameter expansion of the annular bands through the deformable sections, thereby addressing the problem of postoperative variation in a valve-in-valve operations.

20 Claims, 14 Drawing Sheets

(56) References Cited

U.S. PATENT DOCUMENTS

| | | | |
|---|---|---|---|
| 2018/0078366 A1* | 3/2018 | Sievers | A61F 2/2409 |
| 2018/0289475 A1* | 10/2018 | Chung | A61F 2/2445 |
| 2020/0113682 A1 | 4/2020 | Chang et al. | |
| 2021/0015609 A1* | 1/2021 | DuMontelle | A61F 2/2466 |
| 2021/0186689 A1* | 6/2021 | Eidenschink | A61F 2/2409 |

* cited by examiner

SURGICAL PROSTHETIC HEART VALVE

TECHNICAL FIELD

This application relates to the field of medical devices, in particular, to surgical prosthetic heart valves.

BACKGROUND

Aortic valve disease, especially aortic stenosis, has a high mortality rate and brings a huge burden on health care systems around the world. Prosthetic valve replacement is the most common treatment for the diseased aortic valve. Unlike mitral and tricuspid valve disease, the diseased aortic valve is almost always replaced, rather than repaired.

There are two types of methods for biological aortic valve replacement: surgical replacement and transcatheter interventional replacement. Due to lack of long-term durability data for transcatheter valves, young patients (e.g., under 65 years of age) and patients with low surgical risk are often treated by receiving a surgically-replaced heart valve. Currently, surgical valves have a long-term durability in the range of 10 to 20 years. In other words, the surgically-replaced valve may fail during the life cycle of the patient, resulting in the need of another valve replacement. One strategy for treating a failed surgical valve is adopting a valve-in-valve (ViV) intervention procedure. In a valve-in-valve procedure, a new transcatheter interventional heart valve is deployed inside the existing failed surgical valve, thus preventing the patient from suffering another invasive surgical valve replacement procedure.

One of the major challenges with ViV procedures is post-procedural gradients. Expansion of the transcatheter interventional valve (THV) is limited because the THV is deployed into the failed surgical valve, which typically has a non-compliant structure. Due to the thickness of the frame of the THV as well as other structures, the flow orifice of the implanted THV is substantially smaller than the flow orifice of the existing surgical valve. Thus, the implanted THV may suffer from insufficient blood flow, failing to reach the desired valve diameter and thus affecting the opening of the valve leaflets, thereby resulting in adverse effects such as high-pressure gradients, and, more seriously, affecting the service life of the interventional valve.

There are multiple strategies for improving ViV gradients to acceptable levels. One strategy is known as bioprosthetic valve fracture (BVF), or "fracking" as it is commonly referred to. During a BVF procedure, either before or after THV deployment, a high-pressure balloon is inserted into the lumen of the valve or valves and inflated to sufficiently high pressure to break the structure of the failed surgical valve, thereby allowing for greater expansion of the THV. This procedure requires off-label use of a high-pressure balloon, often requiring them to be inflated to 4-times or more their rated burst pressure, thereby increasing patient risk and sacrificing safety. Additionally, the rupture of the failed surgical valve structure during a BVF is rapid and uncontrolled, thus exposing the patient to a high-risk potential for annular rupture. Furthermore, not all surgical valves are capable of being "fracked" in this way.

Another strategy for improved gradients after a ViV is the use of surgically-implanted heart valves that are designed to expand without high pressure BVF during a ViV deployment with a balloon-expandable THV. However, such surgical valves face several challenges which provide opportunities for improvement. First, the cobalt-chrome "stiffener band" only has a single expansion joint. This leads to the possibility of asymmetric expansion during a ViV, creating a possible asymmetric, out-of-round condition, or possible tears of the valve cloth due to the motion of the stiffener band within the cloth during its asymmetric expansion. This could lead to embolization of cloth particles in the case of cloth tears or an asymmetric transcatheter deployment. Additionally, there is no pre-determined expansion limit for the surgical valve. Ideally, a surgical valve optimized for a valve-in-valve deployment would expand by a pre-determined amount and then resist further expansion. This would ensure a high level of radial force between the two prosthetic heart valves and decrease the likelihood of migration or embolization of the THV.

Thus, the ideal surgical valve designed for the potential for an optimal subsequent valve-in-valve procedure would incorporate the following features:

Easily expanded pre- or post-ViV using commercially available balloons at low pressures within their labeled use parameters of pressure.
  Predictable, uniform, controlled expansion around the circumference of the surgical valve, proportional to balloon pressure.
  Predetermined expansion limit to ensure adequate retention force of THV.
  Interlocking features to help retain the THV to prevent migration or embolization.

SUMMARY

The present invention is directed to a novel surgical valve prosthesis for treating aortic valve stenosis and/or regurgitation which attempts to provide the features outlined above.

In order to solve the above technical problems, the present invention provides a surgical prosthetic heart valve having a supporting structure and a plurality of leaflets, the supporting structure generally having an annular shape with a blood flow channel defined in the annular shape, the supporting structure having opposite inflow and outflow sides along an axial direction of the annular shape, with the plurality of leaflets connected to the supporting structure, wherein the supporting structure comprises:

a first annular band, having a plurality of extension bars extending toward the outflow side and spaced from each other in a circumferential direction, and a commissure of adjacent leaflets engaging with the corresponding extension bar; and a second annular band, fixed against an inside or an outside of the first annular band, with the second annular band being adjacent to the inflow side of the first annular band; and wherein both of the first annular band and the second annular band are provided with deformable sections spaced from each other in the circumferential direction for allowing diameter expansion of the respective annular bands.

As set forth below, alternatives and modifications are provided, but not as additional limitations to the above-mentioned subject matter, but merely as further additions or modifications.

Optionally, the deformable sections of the two annular bands are aligned with each other in position in the circumferential direction.

Optionally, each of the annular bands has an opened circuitous configuration in some sections which serve as the deformable sections.

Optionally, the two annular bands are connected with pulling members, and connecting portions of the pulling members are adjacent to the deformable sections of the annular bands.

Optionally, the deformable sections of the first annular band are in one-to-one correspondence with the extension bars in position in the circumferential direction.

Optionally, each of the annular bands has a normal configuration under physiological stress after implantation in the human body, and a diameter expanded configuration expanded under stress greater than physiological stress, and wherein the deformable sections of the second annular band in the diameter expanded configuration are inclined toward the blood channel relative to the normal configuration.

Optionally, the surgical prosthetic heart valve further comprises a metal frame surrounding the blood channel, and rims of the leaflets comprise enclosed fixing rims for connecting with the metal frame and movable rims which are located in the blood channel, and wherein the movable rims of adjacent leaflets are joined to each other.

Optionally, a sewing ring is fixed at the inflow side of the supporting structure, and the annular bands and the sewing ring are entirely covered by a first covering layer.

Optionally, the metal frame is entirely covered by a second covering layer.

Optionally, the metal frame is abutted on the outflow side of the first annular band.

Optionally, the shape of the metal frame is adapted to the shape of the edge of the outflow side of the first annular band.

Optionally, the extension bar has threading holes.

Optionally, with regard to the overall shape of the annular band, the edges at the outflow side of the connecting portions of the first annular band between two adjacent extension bars are smoothly curved.

Optionally, the edges at the outflow side of the corresponding portions of the second annular band are smoothly curved.

Optionally, the two annular bands can be formed of metal or plastic, and at least one of two annular bands is made of metal.

Optionally, the strength of the second annular band is higher than the strength of the first annular band.

Optionally, the material of the first annular band is plastic, and the material of the second annular band is metal.

Optionally, the material of the first annular band is one or more of ABS plastic, acrylic resin, polyvinyl chloride, polycarbonate, polypropylene, polyethylene, polyoxymethylene, polyamide, fluorinated ethylene propylene, polyetherimide, polyetheretherketone, polytetrafluoroethylene, polyester, and polysulfone.

Optionally, the material of the second annular band is one or more of stainless steel, titanium alloy, cobalt-based alloy and nickel-titanium alloy.

Optionally, the annular bands are independently formed as one piece in the form of a ring, or formed by enclosing a strip with both ends of the strip overlapped with each other and fixed by welding.

Optionally, the circuitous configuration is opened at least toward the inflow side.

Optionally, the circuitous configuration is opened only toward the inflow side.

Optionally, in the normal configuration with the diameter unexpanded, the circuitous configuration has a pathway that turns at least 120 degrees.

Optionally, in the normal configuration with the diameter unexpanded, the circuitous configuration has a pathway that turns at least 180 degrees.

Optionally, an area surrounded by the circuitous configuration is configured as an opened area, and along the axial direction of the supporting structure, the opened area of the first annular band is longer than the open area of the second annular band.

Optionally, in the axial direction of the supporting structure, the ratio of the length L1 of the opened area of the first annular band to the length L2 of the opened area of the second annular band in the normal configuration ranges from 1.1 to 3.

Optionally, the ratio of L1:L2 ranges from 1.1 to 2.

Optionally, the number of deformable sections on the annular bands are the same, and in the range of 2 to 6.

Optionally, the deformable sections on the same annular band have the same structure.

Optionally, the deformable sections are evenly spaced with each other on the corresponding annular band.

Optionally, the number of deformable sections on the second annular band is an integer multiple, such as 1 to 3 times, of the number of deformable sections on the first annular band.

Optionally, the circuitous configuration comprises one or more unit regions distributed in succession along the circumferential direction of the supporting structure, each unit region having the same or different shape, and each unit region being independently configured in an Ω-shape, an N-shape, a W-shape, an M-shape or a V-shape.

Optionally, the unit regions are formed as an asymmetrical structure in the axial direction of the supporting structure.

Optionally, the unit regions are symmetrically arranged in the circumferential direction of the annular band.

Optionally, the first annular band is provided with elongated deformable releasing openings at the inflow side of the extension bars, and the circuitous configuration surrounds the respective deformable releasing opening.

Optionally, the deformable releasing opening extends in the same width.

Optionally, the ratio of the length to the width of the deformable releasing opening ranges from 5:1 to 100:1.

Optionally, the ratio of the length to the width of the deformable releasing opening ranges from 10:1 to 80:1.

Optionally, the deformable releasing opening extends in the axial direction of the extension bar.

Optionally, the circuitous configuration on the second annular band is partially or entirely Ω-shaped, with two everted ends opposite to each other at the outflow side, and a curved top end at the outflow side.

Optionally, the number of deformable sections on each of the annular bands is the same as the number of the leaflets.

Optionally, the number of the deformable sections on each of the annular bands is the same as the number of the extension bars and the deformable sections on each of the annular bands correspond to the extension bars in position.

Optionally, an angle of each of the deformable sections relative to an axis of the supporting structure is a central angle of the deformable section, and the central angle of the deformable section ranges from 5 degrees to 30 degrees.

Optionally, the sum of the central angles of the deformable sections on a single annular band is less than or equal to 100 degrees.

Optionally, each deformable section has a single-layer structure in the radial direction.

Optionally, the pulling members are distributed on the deformable sections of the two annular bands.

Optionally, the pulling members are distributed only on the deformable sections of the two annular bands.

Optionally, the pulling member is configured as a rigid member, and the pulling members may be set in pairs, and the two sides of each deformable section in the circumferential direction are provided with a pair of pulling members.

Optionally, the pulling member is configured as a flexible member, and binds and thus fixes the two annular bands.

Optionally, at least one annular band is provided with connecting holes for the pulling member passing through.

Optionally, the connecting holes are respectively provided on two sides of the deformable releasing opening of the first annular band.

Optionally, the second annular band has supporting pieces extending toward the outflow side on both sides of the deformable section in the circumferential direction.

Optionally, the inflow side of the extension bar of the first annular band is configured as a triangular region, and the deformable section of the second annular band together with the supporting pieces on both sides thereof are abutted against the triangular region in the normal configuration.

Optionally, along the axial direction of the supporting structure, the deformable section on the second annular band is higher than the supporting pieces on both sides of the deformable section.

Optionally, slit openings are defined between the deformable section of the second annular band and the supporting pieces on both sides thereof, which open toward the outflow side.

Optionally, the inflow side of the slit opening is closed, and the inner edge of the closed portion is arc-shaped.

Optionally, the deformable sections of at least one of the first annular band or the second annular band allow for expansion thereof while defining a maximum expansion diameter for the at least one of the first annular band or the second annular band.

Optionally, the deformable sections of at least one of the first annular band or the second annular band experiences a three-dimensional twist when it is expanded.

The present invention achieves the diameter expansion of the annular bands through the deformable sections, which also act to define a maximum expansion diameter, thereby solving the problem of postoperative variation in the valve-in-valve operation and effectively improving the therapeutic effect.

Specific advantageous technical effects will be further explained in connection with specific structures or steps in the detailed description.

BRIEF DESCRIPTION OF THE DRAWINGS

FIG. 1b is an enlarged sectional view of a configuration at the position indicated by the letter C in FIG. 1a;

FIG. 1c is an enlarged sectional view of an alternative configuration at the position indicated by the letter C in FIG. 1a;

FIG. 3a is a perspective view of one embodiment of a second annular band that can be used for the heart valve of FIG. 1a;

FIG. 3b is an enlarged view of a deformable section of the second annular band in FIG. 3a;

FIG. 3f is a schematic view showing the deformable section of FIG. 3b in the diameter expanded configuration coupled with the heart valve of FIG. 1a;

FIG. 4b is an enlarged view of a deformable releasing opening of the first annular band in FIG. 4a;

FIG. 5b is a schematic perspective view of one embodiment of a metal frame that can be used with the supporting structure of FIGS. 2 and 5a;

FIG. 9 is an enlarged view of a different embodiment of a deformable section of the second annular band in FIG. 3a.

Figure 1A:
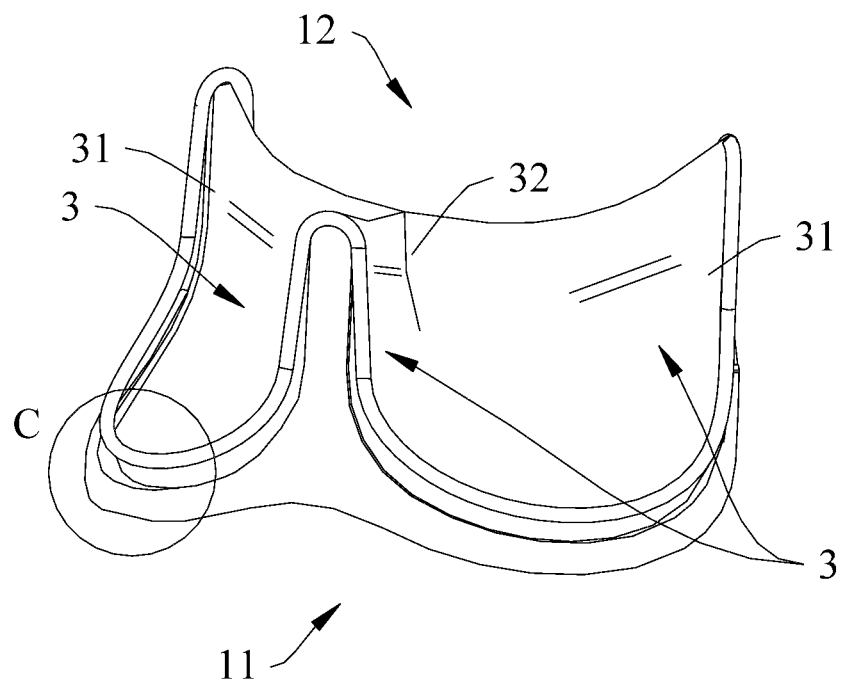
FIG. 1a is a schematic perspective view of a surgical prosthetic heart valve according to one embodiment of the present invention.

List of reference numerals in the drawings: 1, blood channel; 11, inflow side; 12, outflow side; 2, supporting structure; 21, first annular band; 211, extension bar; 2111, triangular region; 212, deformable releasing opening; 213, threading hole; 22, second annular band; 221, deformable section; 2211, first side; 2212, second side; 2213, everted end; 2214, curved top end; 222, supporting piece; 223, slit opening; 23, connecting hole; 24, pulling member; 25, sewing ring; 26, first covering layer; 261, binding region; 3, leaflet; 31, fixing rim; 32, movable rim; 4, metal frame; 41, second covering layer; 5, interventional valve; unit region 27.

DESCRIPTION OF THE EMBODIMENTS

The technical solutions according to the embodiments of the present disclosure will be described in combination with the drawings according to the embodiments of the present disclosure. The described embodiments represent some but not all the possible embodiments.

It should be noted that, when a component is "connected" with another component, it may be directly connected to another component or may be indirectly connected to another component through a further component. When a component is "provided" on another component, it may be directly provided on another component or may be provided on another component through a further component.

Unless otherwise defined, all technical and scientific terms used herein have the same meaning as commonly understood by a person skilled in the art. The terms in the description of the present disclosure are used to describe specific embodiments, and not to limit the present disclosure. The term "and/or" used herein includes any combinations of one or more of the listed options, as well as the combination of all of the listed options.

The present invention describes an embodiment of a surgical prosthetic heart valve, and modifications that can be made thereto. The surgical heart valve of the present invention is primarily adapted for use in valve-in-valve deployment to receive a subsequent THV, although the principles of the present invention can also be applied to other surgical prosthetic heart valves.

Referring to FIGS. 1*a* to 5*a*, one embodiment of the present invention provides a surgical prosthetic heart valve that includes a supporting structure 2 and a plurality of leaflets 3. The supporting structure 2 has a generally annular shape, and a blood flow channel 1 is defined therethrough. The supporting structure 2 has an inflow side 11 and an outflow side 12 opposite to each other in an axial direction of the annular shape. The plurality of leaflets 3 are connected to the supporting structure 2 for controlling blood flow through the blood flow channel 1. The supporting structure 2 includes:

a first annular band 21, having a plurality of extension bars 211 extending toward the outflow side 12 and spaced from each other in a circumferential direction, where a commissure of adjacent leaflets 3 engages with the corresponding extension bar 211;

a second annular band 22, fixed against an inside or outside of the first annular band 21 and adjacent to the inflow side 11 of the first annular band 21. Both of the first annular band 21 and the second annular band 22 have deformable sections 221 spaced from each other in the circumferential direction for allowing diameter expansion of the respective annular bands.

The annular band is expandable through the deformable sections 221. During the valve-in-valve procedure, the diameter expansion of the surgical prosthetic heart valve can be achieved by a self-expandable interventional valve 5 (e.g., a THV), as shown in FIG. 3*f*, or by a separate expansion device. Under a relatively lower pressure (compared to the prior art), the surgical prosthetic heart valve of the present application assumes linear and predictable diameter expansion, and the deformable sections 221 can also limit the tendency to expand after it has completely expanded (or experienced complete deformation), thereby constraining the interventional valve.

Figure 2:
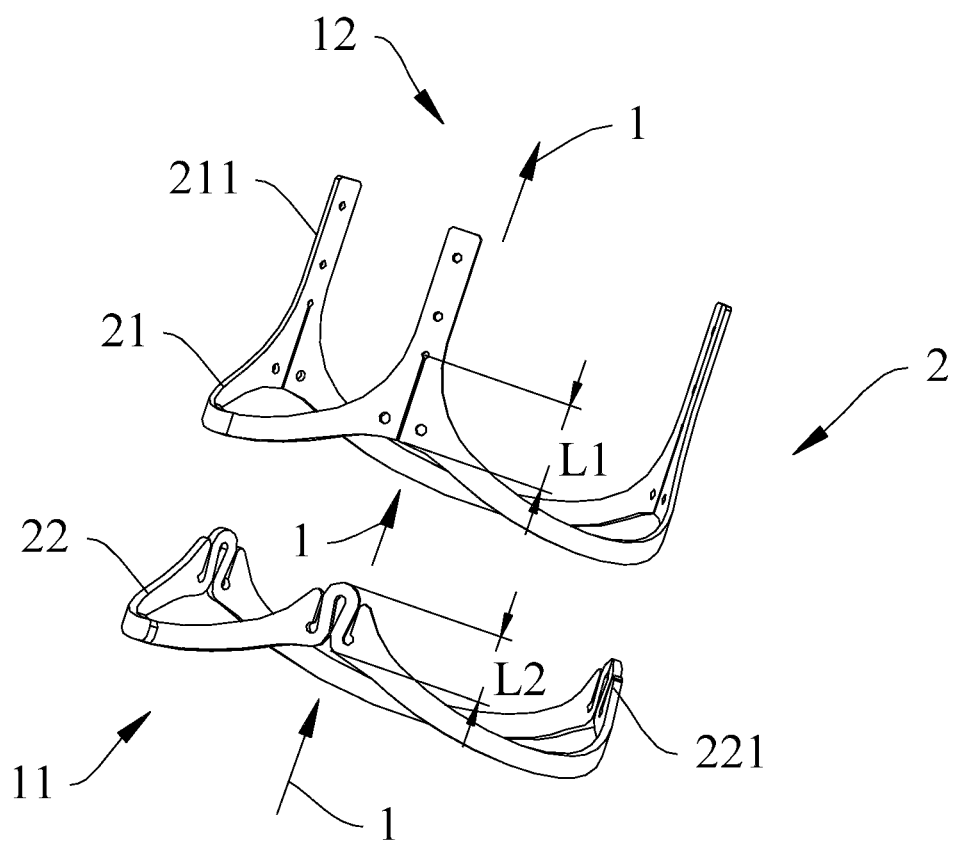
FIG. 2 is an exploded view of one embodiment of a supporting structure that can be used for the heart valve of FIG. 1.
Figure 5A:
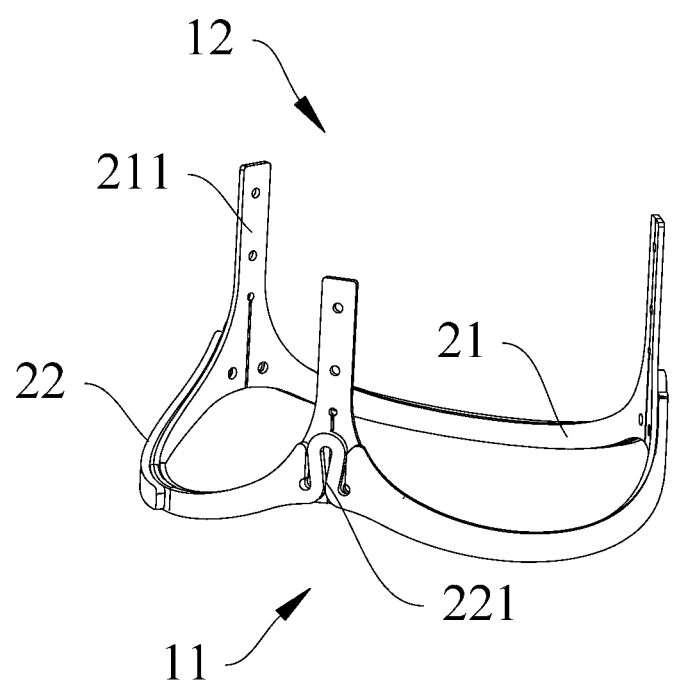
FIG. 5a is a schematic assembled view of the supporting structure of FIG. 2.
Figure 5B:
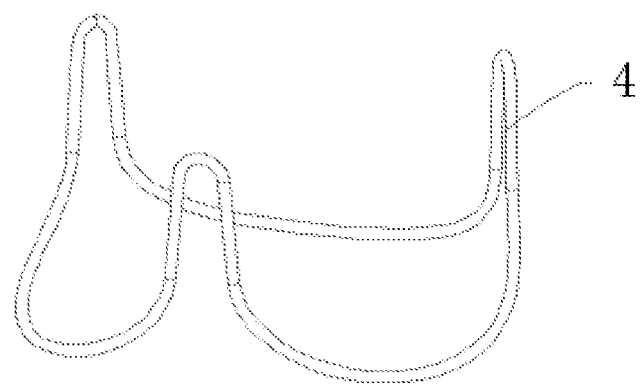
Figure 5C:
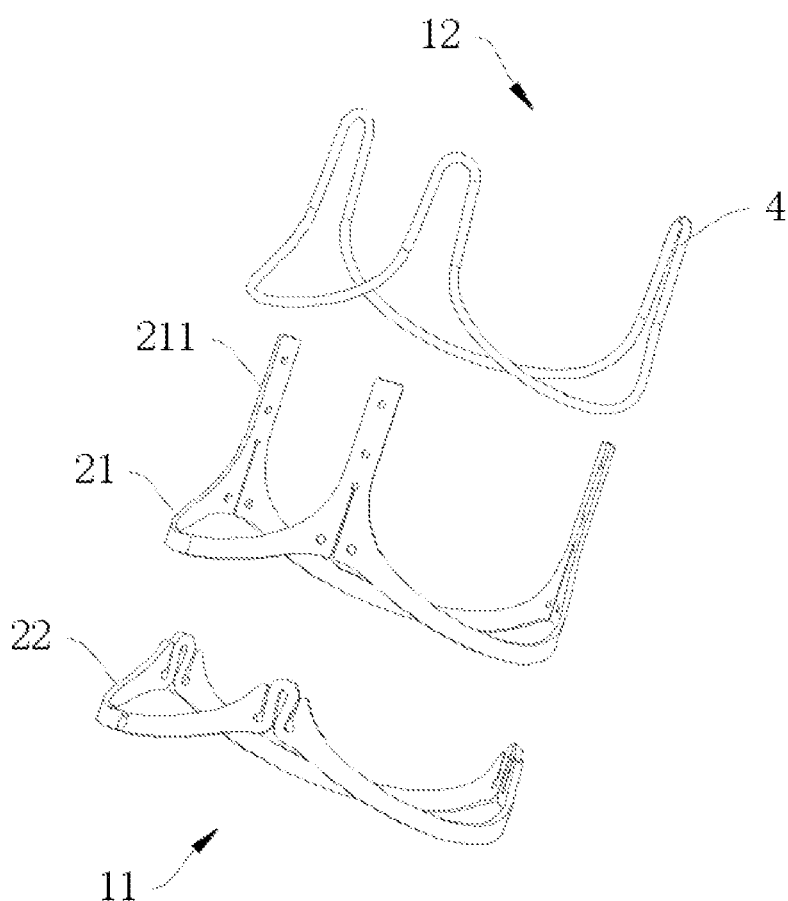
FIG. 5c is an exploded perspective view of the supporting frame of FIGS. 2 and 5a and the metal frame of FIG. 5b.

Referring to FIGS. 2 and 5*c*, the deformable sections 221 of the two annular bands 21 and 22 are positionally aligned with each other in the circumferential direction. Aligning the deformable sections 221 with each other allows the diameter expansion to be accomplished synchronously, and provides a controllable and linear diameter expansion process. At the same time, during the diameter expansion, the portions of the supporting structure 2 which may potentially be displaced are aligned with each other, so that other components can be conveniently installed and connected.

Synchronously releasing the diameter expansion course can be understood from the perspective of the position in the circumferential direction and in the radial direction.

From the perspective of the position in the circumferential direction, the supporting structure 2 is always covered by or installed with other components, and the deformable sections 221 aligned with each other can avoid unnecessary or unexpected drag-in deformation of the components, such as a covering layer and a sewing ring and the like in the circumferential direction. In particular, this avoids an asynchronous deformation process in which one component is deformed while the other is not deformed during the deformation.

From the perspective of the position in the radial direction, the deformable sections 221 during deformation assume a length change of the deformable section itself in the circumferential direction of the annular band, while this length change results in a circumferential change of the overall annular band, which results in a change of the radial position of the deformable sections. In this embodiment, the deformable sections 221 which are aligned with each other are synchronous with each other in their radial positions. At the same time, the supporting structure 2 acts as a frame structure in a three-dimensional space, and the circumferential change of the annular band directly results in a three-dimensional twist of the components in space. In particular, the deformable sections 221 tend to warp relative to the circumferential surface of the annular band, and the deformable sections 221 that are synchronous with each other in positions can be overlapped with each other depending on the superposed warpage tendency thereof, so as to better hold the THV that is introduced later.

In particular, for the understanding of alignment, reference is made to one embodiment, in which each deformable section on the respective annular band has a center position in the circumferential direction, and the center positions of the deformable sections on two annular bands are aligned with each other. In particular, the first annular band 21 is provided with an elongated deformable releasing opening at the inflow side 11 of the extension bar 211, which functions as the deformable section of the first annular band 21, while the deformable section of the second annular band 22 has a configuration with multiple bends or curves (hereinafter referred to as a "circuitous configuration") and forms an opening that opens toward the inflow side 11, wherein the deformable releasing opening is aligned with the opening.

The edges of the first annular band 21 and the second annular band 22 at the outflow sides 12 are approximately aligned with each other. In order to engage with the configuration of the peripheral tissue, both the edges of the first annular band 21 and the second annular band 22 are not configured as a planar circle, but configured as a three-dimensional structure formed by three arc segments connected one after another.

In addition, the deformable sections 221 on the first annular band 21 are, in the circumferential positions, in one-to-one correspondence with the extension bars 211.

Since the commissure of the adjacent leaflets 3 engages with the corresponding extension bar 211, the locations where deformation occurs are mainly concentrated at the commissures of the adjacent leaflets 3 in the circumferential direction during the diameter expansion and deformation of the annular bands, with a relatively small dragging force on the leaflets, which can avoid the risk of the leaflets being torn or even partially falling off.

The supporting structure 2 acts as a frame structure in a three-dimensional space, and the circumferential change of the annular band directly results in a three-dimensional twist of the components in space. In the case where the first annular band 21 is located on the inflow side of the extension bars 211, the length change of the first annular band 21 directly causes the extension bars 211 to have a tendency of closing towards each other at the outflow sides thereof. That is, the extension bars 211 assume an inward inclination. The one-to-one correspondence between the deformable sections 221 and the extension bars 211 in the circumferential positions can synchronize the movements of the two annular bands along with the inward inclination tendency of the extension bars 211, thereby ensuring the two annular bands are in contact with each other in a diameter expanded configuration. Furthermore, the inward warpage configurations of the two annular bands are also allowed to overlap with each other.

Each annular band has a normal configuration under physiological stress after implantation in the human body and a diameter expanded configuration expanded under a stress greater than physiological stress. The deformable sections 221 of the second annular band 22 in the diameter expanded configuration are inclined toward the blood flow channel 1 relative to the normal configuration.

Figure 3A:
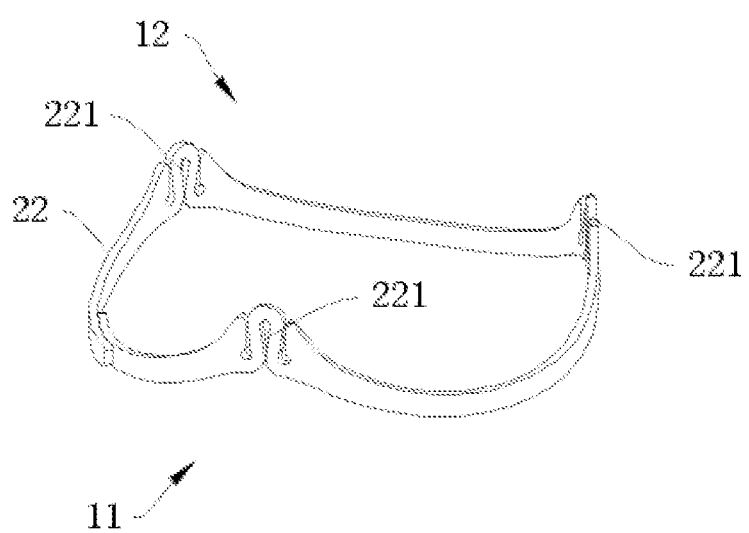
Figure 3B:
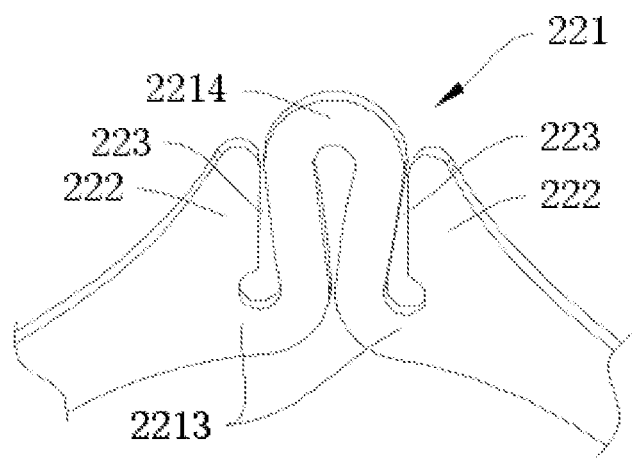
Figure 3C:
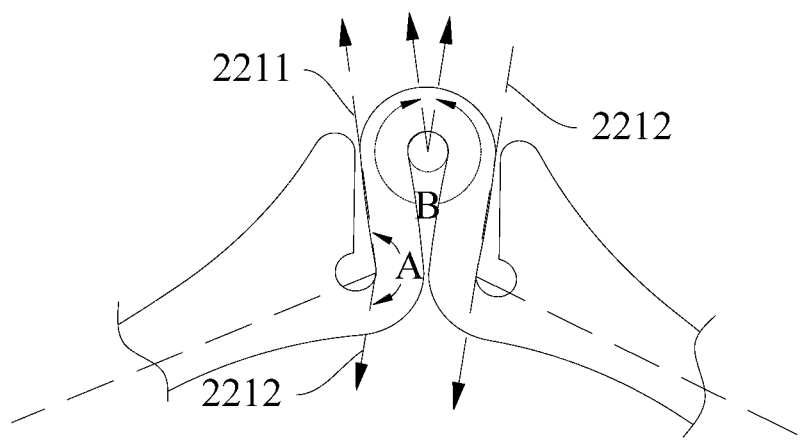
FIG. 3c is a schematic view of the deformable section of the second annular band in FIG. 3a shown with angle annotations.
Figure 3D:
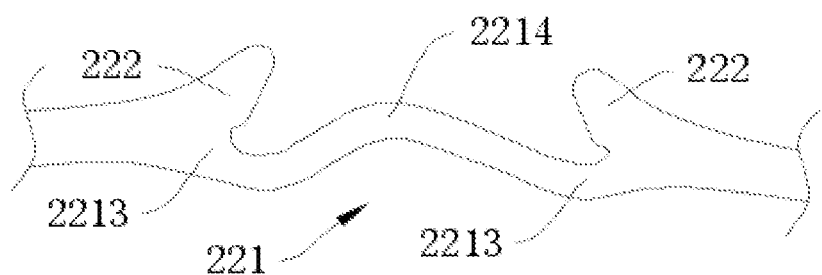
FIG. 3d is a schematic view of the deformable section of the second annular band in FIG. 3a shown in a diameter expanded configuration.
Figure 3E:
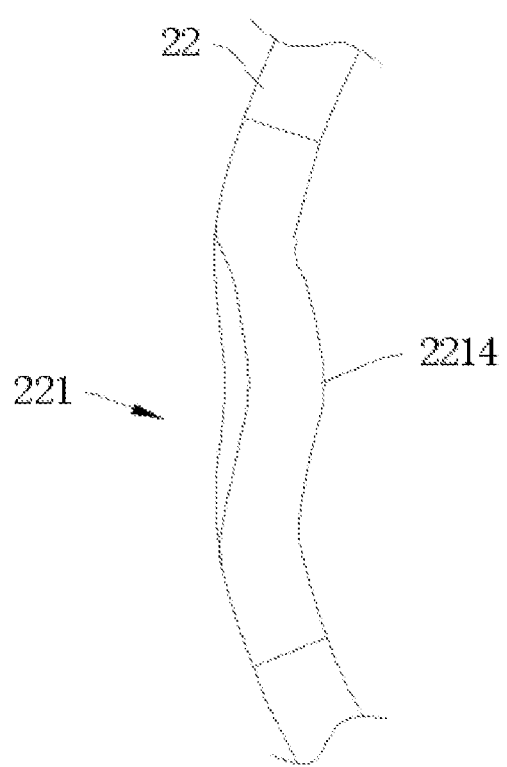
FIG. 3e is another view of the deformable section of FIG. 3d in the diameter expanded configuration.
Figure 3F:
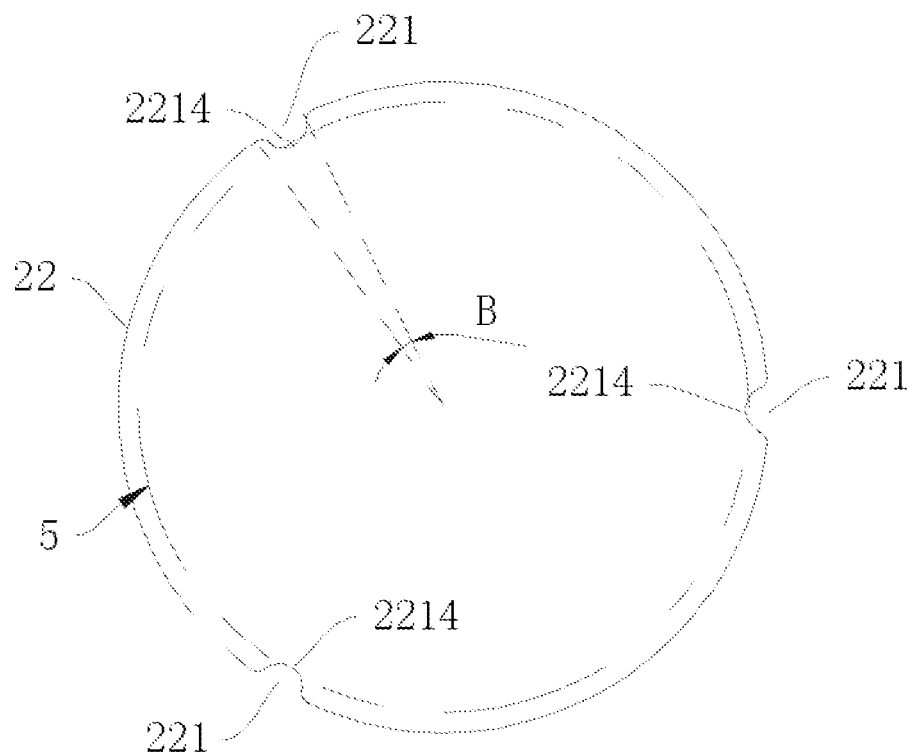

The emphasis in this embodiment is on the fact that the deformable section 221 has a twist out of the plane (i.e., three-dimensional twist) where it is located during diameter expansion, which occurs during expansion of the second annular band 22, such as during the process of a valve-in-valve operation. The twist out of the plane of the deformable section 221 is best shown in FIGS. 3e and 3i, and allows the deformable section 221 to provide an increased holding force to the interventional valve 5. Referring to FIG. 3e, the deformable section 221 is twisted inward so that its curved top end 2214 is moved slightly inwardly.

Compared with the prior art, in the present embodiment, the twist of the deformable sections 221 improves the ability of the surgical valve to position a subsequent interventional valve 5, which further improves the safety of the valve-in-valve operation.

Referring to the FIGS. 5b to 5f, the surgical prosthetic heart valve further includes a metal frame 4 surrounding the blood flow channel 1. Referring also to FIG. 1a, the rims of the leaflets 3 include enclosed fixing rims 31 and movable rims 32, where the fixing rims 31 are connected to the metal frame 4, the movable rims 32 are located in the blood flow channel 1, and the movable rims 32 of two adjacent leaflets 3 are joined with each other.

The fixing rim 31 may be engaged with the metal frame 4 by means of a fixed connection such as sewing or bonding. Alternatively, the fixing rim 31 may be engaged with the metal frame 4 by means of a non-fixed connection such as press-fit, snap-fit, meshing, frictional connection or the like.

Figures 1B, 1C:
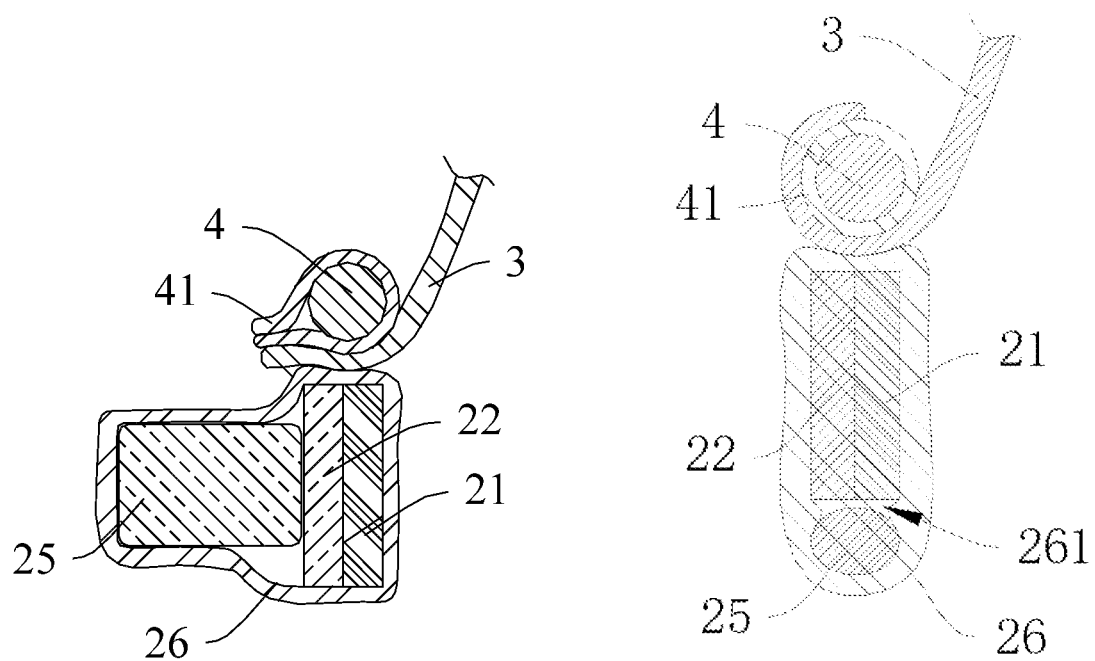

Alternatively, the fixing rim 31 may be engaged with the metal frame 4 by means of other components. Referring to FIGS. 1b and 1c, the metal frame 4 is generally covered by a second covering layer 41. The second covering layer 41 is connected with the leaflets 3 and covers the metal frame 4 so that the fixing rims 31 are connected to the metal frame 4. Similarly, the second covering layer 41 may be mounted to the metal frame 4 by means of the above-mentioned fixed or non-fixed connection techniques.

The inflow side 11 of the supporting structure 2 is fixed with a sewing ring 25, and the annular bands as well as the sewing ring 25, as a whole, are covered by a first covering layer 26. The sewing ring 25 may be located at the outer periphery or at the end surface of the inflow side 11 of the supporting structure 2.

Referring to FIG. 1b, the sewing ring 25 is arranged radially outside of the supporting structure 2. Alternatively, referring to FIG. 1c, the sewing ring 25 is arranged at the axial inflow side of the supporting structure 2. The sewing ring 25 may be a separate component which may be removably mounted at the inflow side 11 of the supporting structure 2 through one of fixed or non-fixed connections described above. The first covering layer 26 tightens the annular bands with the sewing ring 25, thereby improving the integrity. With regard to the mounting method, the first covering layer 26 may tighten the materials by its own wrapping force, and may further tighten the materials by binding through a binding region 261 shown in FIG. 1c. At the same time, an independent constraint space for the sewing ring 25 can be further provided at the binding region 261, thereby further improving the positioning effect.

The sewing ring 25 may be made of an elastic material, such as silicone, or a porous material such as felt, which is mainly used for positioning of the surgical valve to the periphery tissues in vivo for sewing, and can also assist in the prevention of perivalvular leakage. The overall cross-section of the sewing ring 25 may be circular, oval, rectangular, etc. In the present embodiment, the inner and outer positional relationship between the first annular band 21 and the second annular band 22 are not strictly fixed, and thus the inner and outer positional relationship of the two can be adjusted.

With regard to the engagement relationship of the components, the metal frame 4 abuts against the outflow side 12 of the first annular band 21 by welding, connecting through a fastener, or other connecting techniques. Alternatively, the metal frame 4 may be engaged with the first annular band 21 through its own shape configuration. The shape of the metal frame 4 is adapted to the shape of the edge of the first annular band 21 at the outflow side 12. In other words, the profile of the metal frame 4 is fit to the profile of the outflow side 12 of the first annular band 21.

Figure 4A:
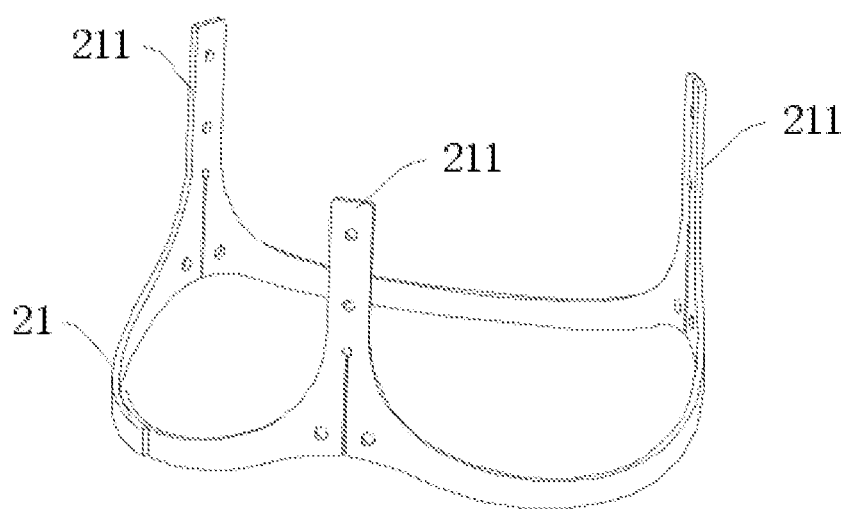
FIG. 4a is a schematic perspective view of one embodiment of a first annular band of the supporting structure in FIG. 2.
Figure 4B:
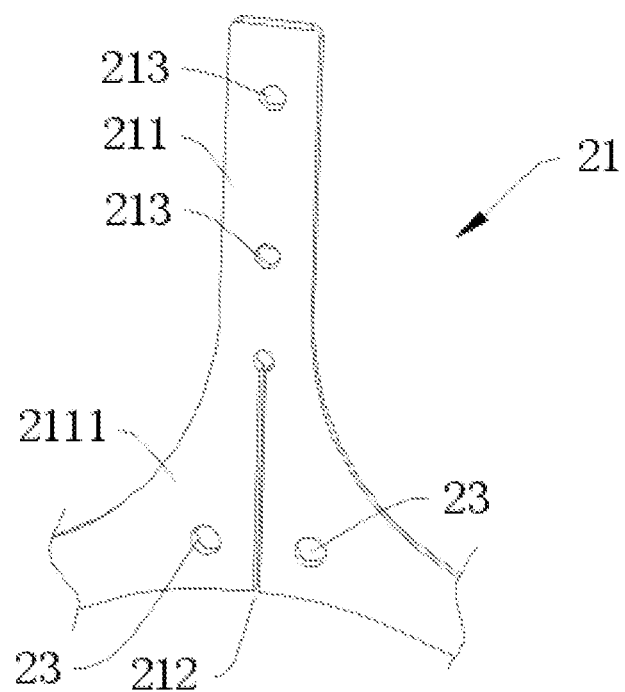
Figure 4C:
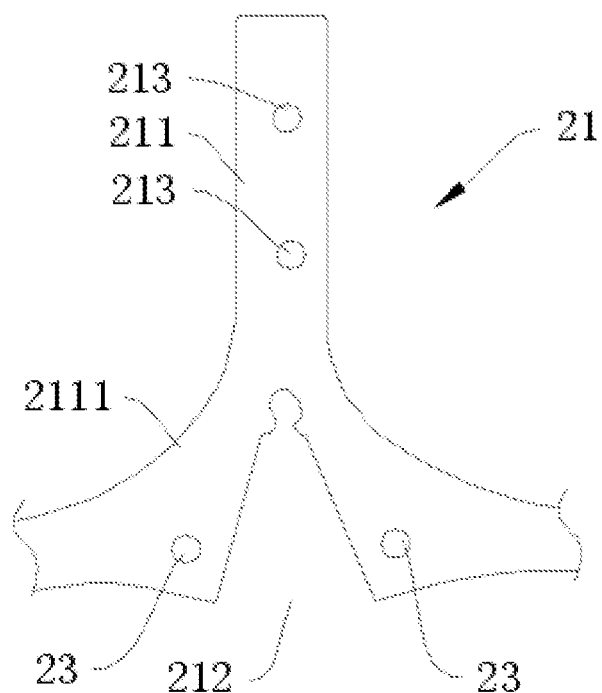
FIG. 4c is a schematic view of the deformable releasing opening of the first annular band in FIG. 4a shown in a diameter expanded configuration.

Referring to FIGS. 4a-4c, the components are connected to each other by means of an elongated constraint element. The extension bar 211 has threading holes 213. The constraint element is capable of threading and binding the components by threading the threading holes 213. The constraint element may, in particular, be a biocompatible fiber and/or plastic rope.

In the overall shape of the annular band, the edges at the outflow side of the portions of the first annular band 21 between two adjacent extension bars are smoothly curved. Similarly, the edges at the outflow side of the corresponding portions of the second annular band 22 are smoothly curved.

The materials of the components should be selected to satisfy the indexes of strength, resistance, biocompatibility and so on. In one embodiment, the materials of the two annular bands are selected from metal and plastic, and at least one of them is metal.

The difference in materials of the two annular bands mainly represents the difference in strength of the two annular bands. In one embodiment, the strength of the second annular band 22 is higher than that of the first annular band 21. The strength here mainly represents the resistance to radial deformation of the supporting structure 2, which can be understood as radial rigidity. During the deformation of the deformable sections 221 driven by the corresponding component, what needs to be resisted is mainly the strength mentioned above. The above-mentioned requirement can be easily met by the provision of specific materials. Specifically, in one embodiment, the material of the first annular band 21 is plastic, and the material of the second annular band 22 is metal. In a particular product, the material of the first annular band 21 is one or more of ABS plastic, acrylic resin, polyvinyl chloride, polycarbonate, polypropylene, polyethylene, polyoxymethylene, polyamide, fluorinated ethylene propylene, polyetherimide, polyetheretherketone, polytetrafluoroethylene, polyester, and polysulfone. Similarly, the material of the second annular band 22 is one or more of stainless steel, titanium alloy, cobalt-based alloy and nickel-titanium alloy.

Figure 3G:
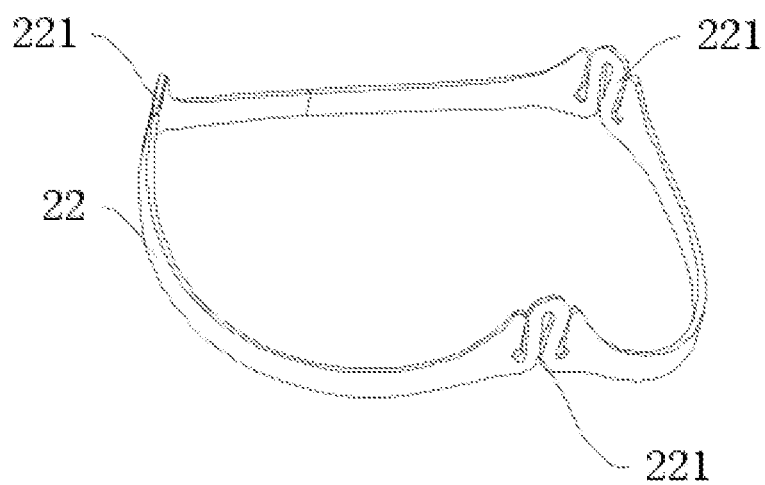
FIG. 3g is a schematic perspective view of another embodiment of a second annular band.
Figure 4D:
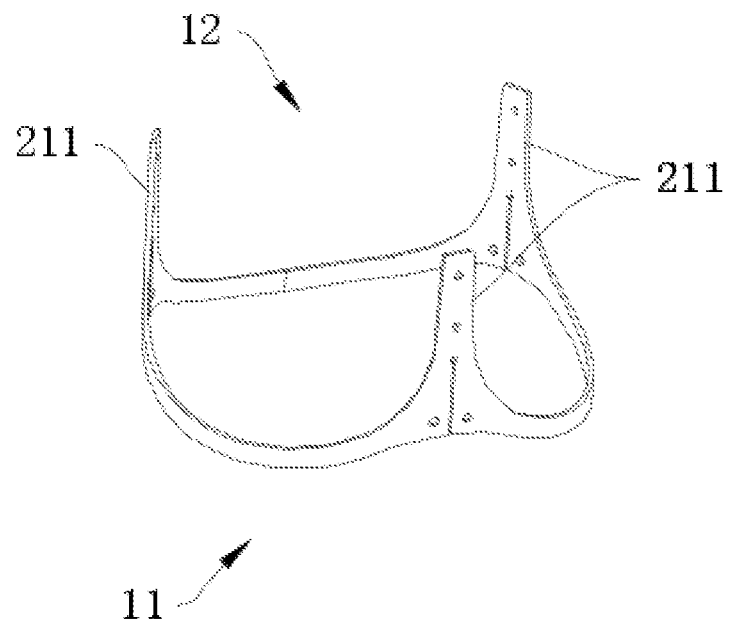
FIG. 4d is a schematic perspective view of another embodiment of a first annular band.

With regard to the specific production method, referring to the embodiments shown in FIGS. 3g and 4d, each of the annular bands is independently formed as one piece in the form of a ring, which can be made by removing material from a cylindrical billet or formed in one piece by powder metallurgy. Alternatively, referring to the embodiments shown in FIGS. 3a and 4a, each of the annular bands is formed by enclosing a strip whose ends overlap each other and are fixed by welding. Plastic components can be obtained by means of injection molding, blow molding, 3D printing, or from a strip whose ends are joined by an adhesive or other bonding method.

To provide the deformable section 221, a weakened structure may be provided. Alternatively, in the embodiments shown in FIGS. 3b and 4b, each of the first and second annular bands 21, 22 has an opened circuitous configuration in some sections which allow for the diameter expansion of the corresponding annular band.

In detail, with reference to the embodiments shown in FIGS. 3a and 5a, the circuitous configurations are opened towards the inflow side 11. Referring to the deformable section 221 for the second annular band 22 (see FIGS. 3c and 3d), the circuitous configuration can be defined as beginning at the everted end 2213 on the left side of FIGS. 3c and 3d, then taking a bend of an obtuse angle A towards a generally straight segment illustrated by a first side 2211, and then a bulbous or curved top end 2214 that takes a 180-degree turn towards an opposite (to the first side 2211) a generally straight segment illustrated by a second side 2212 before taking another bend of an obtuse angle to the other everted end 2213 on the right side of FIGS. 3c and 3d. As such, the circuitous configuration resembles an Ω-shape. Thus, the space between the two straight segments 2211 and 2212 defines an opened area or space. The angle A substantially affects the opening tendency of the circuitous configuration. For a given specific product, in the normal configuration without diameter expansion, the angle A is at least 180 degrees. The shape of the circuitous configuration is also influenced by the central angle B of the circuitous extension course corresponding to its inscribed circle as shown in FIG. 3c. In the embodiment shown in FIG. 3c, the central angle B is equal to or greater than 260 degrees. In a practical product, that corresponding central angle B is equal to or greater than 300 degrees.

Figure 3H:
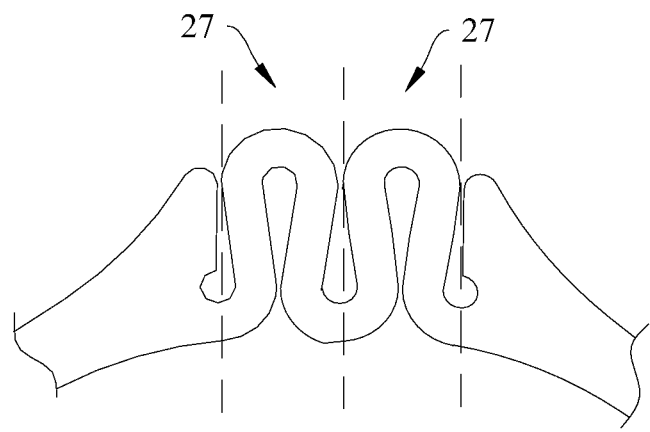
FIG. 3h is a schematic view of an alternative embodiment of a deformable section which includes a plurality of unit regions.
Figure 3I:
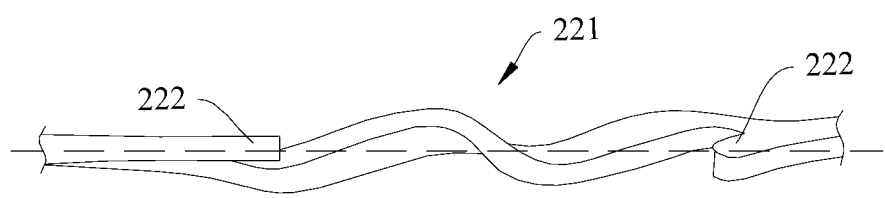
FIG. 3i is a top view of the deformable section of FIG. 3d in the diameter expanded configuration.

Referring to the embodiment shown in FIGS. 3a to 3g, the circuitous configuration is provided with single unit region for deformation. As used herein, the term "unit region" means a single Ω-shaped configuration. In an alternative embodiment shown in FIG. 3h, the circuitous configuration can include a plurality of unit regions 27 arranged in succession along the circumferential direction of the supporting structure 2, where each unit region has the same shape. As shown in FIG. 3h, the circuitous configuration includes two unit regions, with each unit region representing a single Ω-shaped configuration. In other embodiments, each of the unit regions can have different shapes. Each unit region can also be independently configured as an N-shape, a W-shape, an M-shape, or a V-shape, or any other shape that allows for compression and expansion in the manner illustrated in FIGS. 3c and 3d. The unit regions can also be partially overlapped. In terms of the arrangement of the unit regions, the individual unit regions are asymmetric in the axial direction of the supporting structure 2. From the perspective of the deformable sections 221, the plurality of unit regions is symmetric in the circumferential direction of the annular band 22.

Figure 9:

The circuitous configuration for the deformable sections 221 can be inverted. For example, FIG. 9 shows a different embodiment where the single Ω-shaped configuration has been inverted.

Each deformable section in the first annular band 21 is best shown in connection with FIGS. 4b and 4c, and has an elongated deformable releasing opening 212 at the inflow side 11 of the extension bar 211, with a circuitous configuration formed around the deformable releasing opening 212. The circuitous configuration of the deformable releasable opening 212 is best shown in the expanded state in FIG. 4c, and is generally V-shaped with a curved top opening at the apex of the V-shape. When the first annular band 21 is in the compressed state (see FIG. 4b), the deformable releasable opening 212 resembles a slit with the curved top opening almost resembling a circle. The deformable releasing opening 212 extends in the axial direction of the extension bar 211. The axial direction of the supporting structure 2 and the axial direction of the extension bar 211 are parallel to each other. The deformable releasing opening 212 extends with equal width on the supporting structure 2. Further, referring to FIG. 4b, the ratio of length to width for each releasing opening 212 ranges from 5:1 to 100:1, and in a preferred embodiment, the specific ratio of length to width for each releasable opening 212 ranges from 10:1 to 80:1. More preferably, the specific ratio of length to width for each releasable opening ranges from 20:1 to 60:1.

The two different circuitous configurations described above for the two annular bands 21, 22 are just exemplary. In fact, any of the two different circuitous configurations can be independently provided on either of the two annular bands 21, 22. In some embodiments, the two annular bands 21, 22 can have the same circuitous configuration, while in other embodiments, the two annular bands 21, 22 can have different circuitous configurations. No matter which circuitous configuration are used for the two annular bands 21, 22, the detailed structures shown and described herein for the circuitous configurations of the two annular bands 21, 22 can be modified or adjusted. For example, with reference to the embodiment shown in FIG. 2, the area surrounded by the circuitous configuration is an open area, and the open area of the first annular band 21 is longer than the open area of the second annular band 22 in the axial direction of the supporting structure 2. Here, "the open area of the first annular band 21 is longer than the open area of the second annular band 22 in the axial direction of the supporting structure 2" means that the open area of the first annular band 21 is longer than the open area of the second annular band 22 in a direction from the inflow side 11 to the outflow side 12. In the same form of the circuitous configuration, a longer open area means a longer deformation pathway. This deformation pathway refers to the path in which the circumference of the first annular band 21 or the second annular band 22 changes; in other words, the longer the open area of the circuitous configuration, the greater the circumference change of the respective annular band after being deformed. Similarly, the length of the open area may be provided to adapt to the deformation course of the respective circuitous configuration.

The difference in the size of the open area of the first annular band 21 from the open area of the second annular band 22 also makes it possible to synchronize the radial positions of the two annular bands in the diameter-expanded configuration. With regard to the peripheral components, the inflow side 11 of the extension bar 211 of the first annular band 21 is configured as a triangular region 2111, and the deformable section 221 of the second annular band 22, together with supporting pieces 222 on both sides thereof, abut against the internal sides of the triangular region 2111 in the normal configuration. During the deformation of the deformable releasing opening 212, the triangular region 2111 tends to warp relative to the circumferential surface of the annular band 21, and the warpage tendency may result in a certain gap between the two annular bands 21, 22 in the diameter expanded configuration. It can be determined from the geometric analysis that the longer the length of the deformable releasing opening 212 in the axial direction of the supporting structure 2, the greater the distance that the warpage of the triangular region 2111 can be uniformly distributed over, thereby reducing the overall warpage tendency, synchronizing the deformation of the two annular bands 21, 22, and keeping the two annular bands in contact. Referring to the annotations shown in FIG. 2, in the axial direction of the supporting structure 2, the ratio between the length L1 of the open area of the first annular band 21 and the length L2 of the open area of the second annular band 22 in the normal configuration ranges from 1.1 to 3. In a preferred embodiment, the ratio of L1 to L2 ranges from 1.1 to 2. In the embodiment shown in the drawings, the specific ratio of L1:L2 ranges from 1.15 to 1.35.

The number of deformable sections of the two annular bands may be equal to each other to facilitate the alignment therebetween. Alternatively, the number of deformable sections 221 on the second annular band 22 may be an integral multiple of the number of deformable sections 221 on the first annular band 21. Depending on the desired application, the integral multiples above may be selected from 1 times, 2 times or 3 times.

In terms of the number of deformable sections, having more deformable sections 221 can allow a greater deformation, while the strength of the supporting structure 2 would be reduced. Referring to one embodiment, the numbers of deformable sections of the annular bands 21, 22 are the same, ranging from 2 to 6. In the exemplary embodiments shown in the drawings, it is shown that each annular band is provided with three deformable sections 221. Having an increased number of deformable sections 221 also makes it difficult to maintain the consistency of the deformable sections 221. The reduced consistency of the deformable sections 221 results in non-synchronization of the deformable sections 221 during the deformation, resulting in a reduced degree of linear variation during the deformation of the supporting structure 2 as a whole. In this embodiment, the deformable sections 221 are identical in structure. Similarly, the deformable sections 221 can be evenly spaced along the corresponding annular band. The evenly spaced arrangement can avoid the influence of other components on the deformation of the deformable sections 221.

The number of deformable sections is the same as the number of the leaflets. In one embodiment, the number of deformable sections is the same as the number of the extension bars 211 and the positions of deformable sections correspond to that of the extension bars 211. Referring to FIG. 3f, the angle of each deformable section relative to the axis of the supporting structure 2 is the central angle B of the deformable section, and the central angle of the deformable section ranges from 5 degrees to 30 degrees. The sum of the central angles of the deformable sections on a single annular band is less than or equal to 100 degrees. As will be understood from the above description, the deformable sections mentioned in the present embodiment have a single-layer structure in the radial direction. Each deformable section is deformable by itself without additional guiding or limiting components. During the deformation, each deformable section is not fractured in the circumferential direction.

Figure 5D:
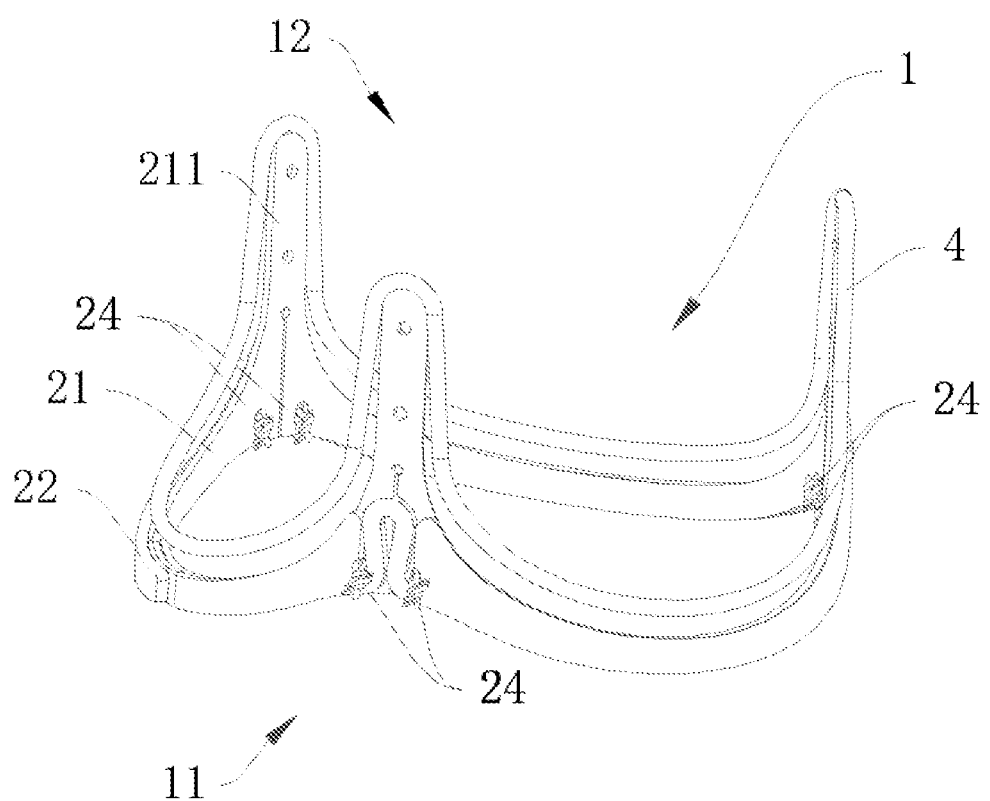
FIG. 5d is a schematic assembled view of a surgical prosthetic heart valve according to another embodiment.
Figure 5E:
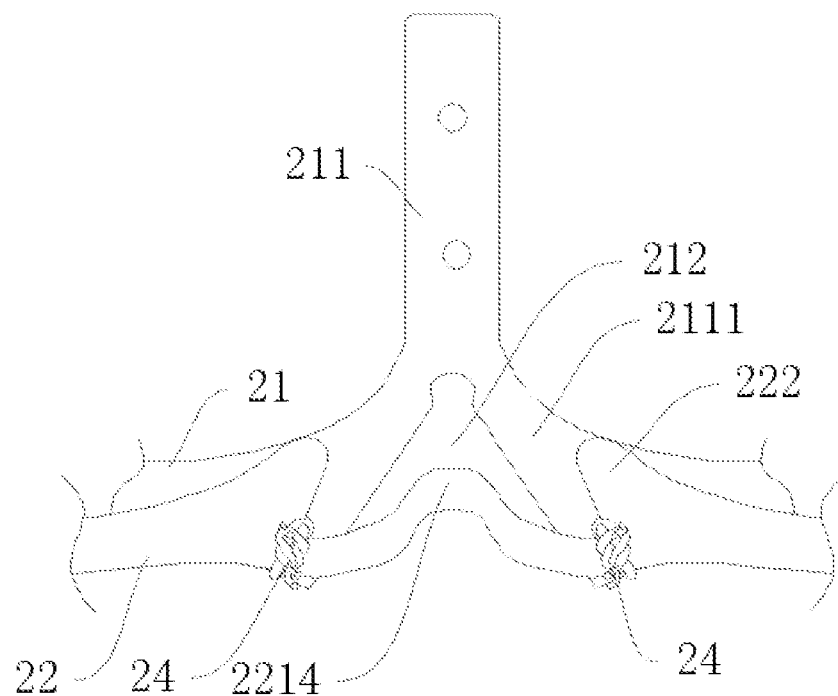
FIG. 5e is a schematic view of pulling members during diameter expansion according to the embodiment of FIG. 5d.
Figure 5F:
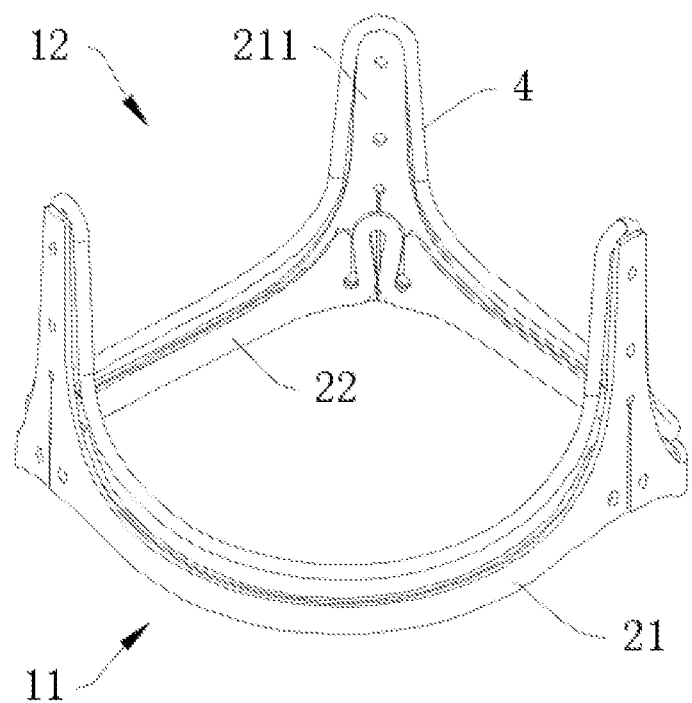
FIG. 5f is a schematic assembled view of a surgical prosthetic heart valve according to another embodiment.

Referring to FIG. 5d, in another embodiment of the present invention, the first annular band 21 and the second annular band 22 are the same as in FIG. 2, except that the two annular bands 21 and 22 are connected through pulling members 24, and the connecting portions for the pulling members 24 are adjacent to the deformable sections 221 of the annular bands.

The pulling members 24 are synchronized with the deformation positions and deformation amounts of both the first annular band 21 and the second annular band 22 so as to avoid unexpected displacement after deformation.

Other than the covering layer, the first annular band 21 and the second annular band 22 may be connected to each other by pulling members 24. Referring to the embodiments shown in FIGS. 5e and 5f, the first annular band 21 and the second annular band 22 are connected with pulling members 24. The distribution of the pulling members 24 affects the function of the pulling members 24 to the annular bands. For example, in the present embodiments shown in FIGS. 5d and 5e, the pulling members 24 are distributed adjacent to the deformable sections 221 of the annular bands, and function to synchronize the deformations of the deformable sections 221 of the annular bands. In other embodiments, the pulling members can be arranged at other positions, such as at the deformable sections, of the first and second annular bands 21 and 22. In addition to synchronizing the deformations of the deformable sections 221 of the respective annular bands, the pulling members 24 may restrict the independent motions of the respective annular bands 21 and 22, so that the pulling members 24 are preferably only distributed at the deformable sections 221 of the annular bands, in order to avoid an excessive restraint from the pulling members 24.

In one of the embodiments, the pulling member 24 is configured as a rigid member, and is made of material such as plastic, metal, or alloy or the like.

Alternatively, in another embodiment, the pulling member 24 is configured as a flexible member and binds and therefore fixes the two annular bands, and is made of a material such as natural or synthetic fiber and/or tethers.

In order to ensure the pulling effect, the pulling members 24 may be set in pairs, and the two sides of each deformable section 221 in the circumferential direction are provided with a pair of pulling members 24.

The annular band needs to provide a mounting position for the pulling member 24 to improve the mounting effect. In one embodiment, at least one of the annular bands 21 is provided with connecting holes 23 for the pulling member 24 to pass through. The connecting holes 23 can provide a constraint for the pulling member 24. Structurally, the connecting hole 23 may be configured as a through-hole that is circumferentially closed and extends axially through the annular band 21, or a constraint hole that is circumferentially opened and extends axially through the annular band 21, or as a blind hole that is circumferentially and axially closed, or a constraint hole that is circumferentially opened and axially closed. The specific configuration of the connecting hole 23 may be provided depending on different pulling members 24 and different fixing parameters selected for a given application. The inner edge of each connecting hole 23 is preferably configured as a smooth curve, for example, the connecting hole 23 may be configured as a circular hole or an oval hole.

The design of the pulling member 24 has the following advantage: based on the connection strength provided by the pulling member 24, the supporting frame for the surgical valve can expand consistently and uniformly under the action of an external force, which allows a uniform, symmetric and predictable expansion during a valve-in-valve surgical procedure.

The connecting holes 23 may be arranged in multiple locations on the annular band 21. Alternatively, two sides of the deformable releasing opening 212 on the first annular band 21 are respectively provided with a connecting hole 23. Similarly, the second annular band 22 may also be provided with connecting holes 23 at corresponding positions. Further, the connecting holes 23 of the first annular band 21 and the connecting holes 23 of the second annular band 22 are aligned with each other.

In the present embodiment, the inner and outer positional relationship between the first annular band 21 and the second annular band 22 are not strictly fixed, and thus the inner and outer positional relationship of the two can be adjusted. The embodiment shown in FIG. 5f may employ the same principles that are shown and described in connection with FIG. 5d, and thus will not be described here.

Referring to FIG. 3b, the second annular band 22 has supporting pieces 222 extending in the circumferential direction toward the outflow side 12 on both sides of the deformable section 221. The supporting pieces 222 can further control the deformation process of the deformable sections 221. Along the axial direction of the supporting structure 2, the deformable section 221 on the second annular band 22 can extend to a position that is higher than the highest point of the supporting pieces 222 on both sides thereof. Slit openings 223, which are opened toward the outflow side 12, are defined between the deformable section 221 of the second annular band 22 and the supporting pieces 222 on both sides thereof for the cooperation therebetween. The inflow side 11 of the slit opening 223 is closed, the inner edge of the closed portion is arc-shaped, with the slit opening 223 narrowing as it extends towards the outflow side 12. The slit opening 223 allows for the relative movement of the deformable section 221 and the supporting pieces 222, and also provides a structural base for other functions. For example, in one embodiment, the slit opening 223 may be configured as the connecting hole 23 for connecting the pulling member 24. The pulling member 24 functions to connect the first annular band 21 and the second annular band 22.

In addition to cooperation with the deformable section 221 of the second annular band 22, the supporting piece 222 can also cooperate with the first annular band 21. For example, the inflow side 11 of the extension bar 211 of the first annular band 21 is configured as a generally triangular region 2111. See FIG. 4b. In the normal configuration, the deformable section 221 of the second annular band 22, together with the supporting pieces 222 on both sides thereof, abut against the triangular region 2111.

In the present disclosure, the design of the deformable sections 221 allows a controllable, uniform, and symmetrical expansion of the surgical valve under desired operation conditions. The deformable sections 221 should be designed in length, shape and material to ensure that the deformable sections 221 allow the first annular band 21 and the second annular band 22 to expand when a balloon or other mechanism applies sufficient radial force to the surgical valve. The deformable section 221 has a normal configuration and is gradually deformed as the circumference of the first annular band 21 and the second annular band 22 increases. As shown in FIG. 3d, the deformable section 221 deforms to be gradually straightened. After the deformable section 221 is completely released and expanded, the deformable section 221 fixes the circumferences of the first annular band 21 and the second annular band 22, thereby preventing further expansion. In this regard, the deformable section 221 defines a maximum expansion diameter which is the limit for expansion.

Figure 6:
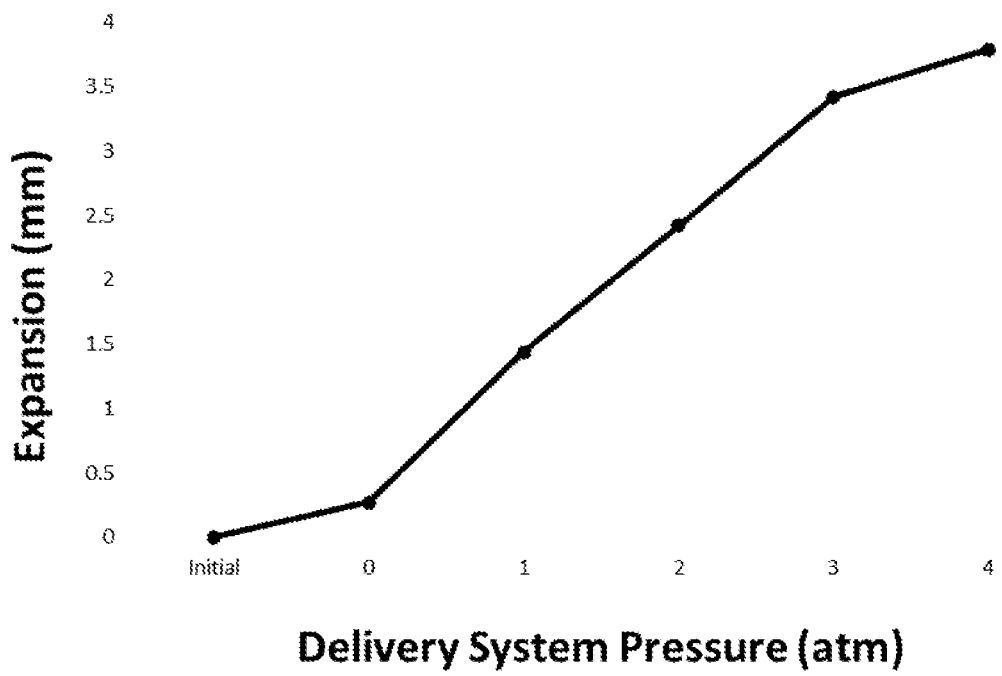
FIG. 6 is a schematic diagram showing the relationship between the internal pressure of the expanded device and the expansion of the deformable sections according to one embodiment.

The balloon or another mechanism can be used to apply a radial force to the surgical heart valve by pressure expansion, and the relationship between pressure and the expansion of the deformable sections 221 can be obtained as shown in the graph of FIG. 6. In this drawing, the horizontal ordinate represents the radial expansion pressure provided by the delivery system, in a standard atmospheric pressure of atm, and the vertical coordinate represents the expansion of the deformable section 221, in mm, wherein:

in the initial stage, at a pressure of 0 atmosphere, the surgical valve has slightly expanded due to radial forces generated by the self-expandable interventional device deployed in the annular bands;

in the expansion stage, the deformable sections 221 are deformed to expand the annular bands under the pressure of the balloon; and in the end stage, after the pressure reaches 3 atmospheres, the deformable sections 221 have completely expanded, and begin to prevent further expansion, in particular, when the pressure reaches from 3 to 4 atmospheres, the variation of the expansion of the deformable sections 221 is significantly smaller than that in the expansion stage.

Figure 7:
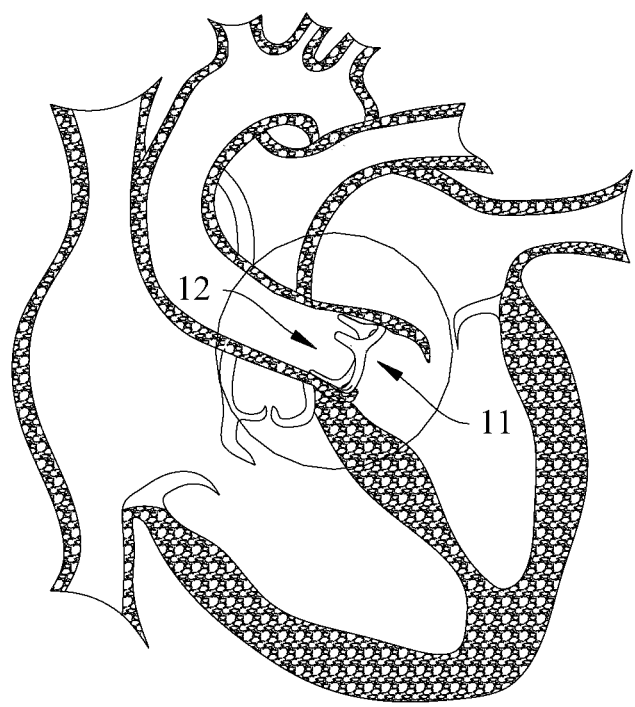
FIG. 7 schematically shows the surgical prosthetic heart valve of the present invention deployed in a valve annulus of a heart.
Figure 8:
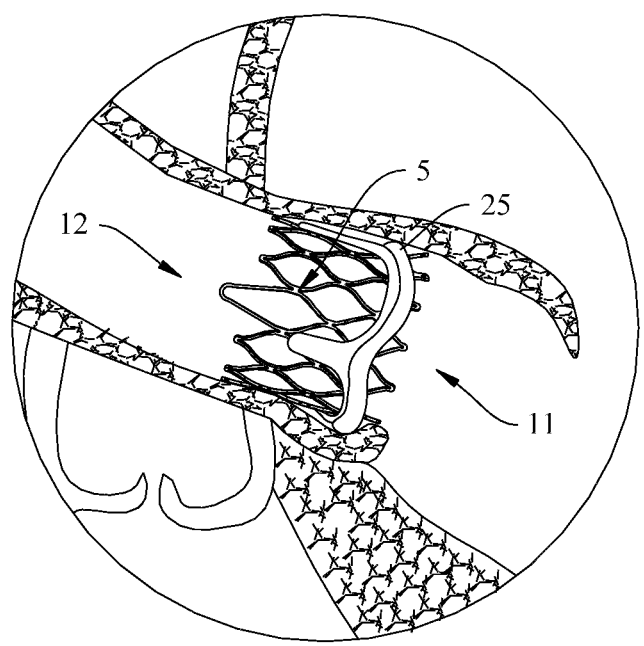
FIG. 8 schematically shows an interventional valve subsequently deployed in the surgical prosthetic heart valve shown in FIG. 7.

FIG. 7 illustrates the supporting structure 2 of a surgical heart valve according to FIGS. 1a-5c deployed at the aortic annulus of a human heart. When this surgical heart valve becomes defective and a THV 5 is needed, a new THV 5 can be delivered in a minimally-invasive manner and secured inside the supporting structure 2. This is shown in FIG. 8. The present invention provides a surgical heart valve that can be expanded without fracturing any of the components of the surgical heart valve, and will expand in a predictable and linear manner when pressure is applied with a balloon or other mechanism, so that the surgeon who is conducting the subsequent valve-in-valve procedure can stably expand the surgical heart valve with a higher degree of safety compared to the prior art heart valves that may hydraulically fracture the already-implanted surgical valve, thereby avoiding sudden, uncontrolled expansion of the surgical heart valve at a very high pressure.

The features described in the above various embodiments may be combined. In order to simplify the descriptions, not all possible combinations of the features in the above embodiments have been described. However, any combinations of the features should be within the scope of the disclosure as long as no conflict resides between these features. In the case where the features in different embodiments are shown in the same drawing, it may be considered that this drawing discloses a combination of the various embodiments involved.

The above embodiments are only several implementations of the present application which are described specifically and in detail, without limitation to the scope claimed by the present disclosure. Those skilled in the art can make various modifications and variations to the embodiments without departing from the spirit and scope of the present disclosure, and these modifications and variations should fall into the scope claimed by the present disclosure.

What is claimed is:

1. A surgical prosthetic heart valve, comprising a supporting structure and a plurality of leaflets, the supporting structure generally having an annular shape with a blood flow channel defined in the annular shape, the supporting structure having opposite inflow and outflow sides along an axial direction of the annular shape, the plurality of leaflets connected to the supporting structure, wherein the supporting structure comprises:
   a first annular band, having a plurality of extension bars extending toward the outflow side and spaced from each other in a circumferential direction, the first annular band having first deformable sections, with each first deformable section positioned at one of the plurality of extension bars, and wherein each first deformable section is opened only toward the inflow side;
   a second annular band, fixed against an inside or an outside of the first annular band, the second annular band being adjacent to the inflow side of the first annular band, the second annular band having second deformable sections spaced from each other in the circumferential direction;
   a commissure of adjacent leaflets engaging with the corresponding extension bars; and
   wherein the first and second deformable sections are aligned with each other in the circumferential direction;
   wherein the deformable sections of at least one of the first annular band or the second annular band experiences a three-dimensional radial inward twist when the deformable sections of at least one of the first annular band or the second annular band are expanded.

2. The surgical prosthetic heart valve of claim 1, wherein the number of deformable sections on each of the annular bands is the same as the number of the leaflets.

3. The surgical prosthetic heart valve of claim 1, wherein the number of the deformable sections on each of the annular bands is the same as the number of the extension bars.

4. The surgical prosthetic heart valve of claim 1, wherein each of the annular bands has opened areas in some sections which serve as the deformable sections.

5. The surgical prosthetic heart valve of claim 4, wherein the opened areas are opened toward the inflow side.

6. The surgical prosthetic heart valve of claim 4, wherein each opened area comprises one or more unit regions distributed in succession along the circumferential direction of the supporting structure, each unit region being the same or different in shape, and each unit region being independently configured in an Ω-shape, an N-shape, a W-shape, an M-shape or a V-shape.

7. The surgical prosthetic heart valve of claim 6, wherein each of the one or more unit regions form an asymmetrical structure in the axial direction of the supporting structure.

8. The surgical prosthetic heart valve of claim 4, wherein the first annular band is provided with elongated deformable releasing openings on the inflow side of the plurality of extension bars.

9. The surgical prosthetic heart valve of claim 4, wherein the opened areas on the second annular band are partially or entirely Ω-shaped, with two everted ends opposite to each other at the inflow side, and a curved top end at the outflow side.

10. The surgical prosthetic heart valve of claim 4, wherein along the axial direction of the supporting structure, the opened area of the first annular band is longer than the opened area of the second annular band.

11. The surgical prosthetic heart valve of claim 1, wherein an angle of each of the deformable sections in the second annular band_relative to an axis of the supporting structure is a central angle of the deformable section, and the central angle of the deformable section ranges from 5 degrees to 30 degrees.

12. The surgical prosthetic heart valve of claim 1, wherein each of the annular bands has a normal configuration under physiological stress after implantation in the human body and a diameter expanded configuration expanded under stress greater than physiological stress, and wherein the deformable sections of the second annular band in the diameter expanded configuration are inclined toward the blood channel relative to the normal configuration.

13. The surgical prosthetic heart valve of claim 1, wherein both sides of the deformable section of the second annular band in the circumferential direction are respectively provided with a supporting piece extending toward the outflow side.

14. The surgical prosthetic heart valve of claim 13, wherein slit openings are defined between the deformable section of the second annular band and the supporting pieces on both sides thereof, which open toward the outflow side.

15. The surgical prosthetic heart valve of claim 1, wherein the two annular bands are connected with pulling members, and connecting portions of the pulling members are adjacent to the deformable sections of the annular bands.

16. The surgical prosthetic heart valve of claim 15, wherein the pulling members are distributed at the deformable sections of the two annular bands.

17. The surgical prosthetic heart valve of claim 1, wherein at least one of the two annular bands is of a metal material, and the other of the two annular bands is of a metal or plastic material.

18. The surgical prosthetic heart valve of claim 1, wherein the surgical prosthetic heart valve further comprises a metal frame surrounding the blood channel, and rims of the leaflets comprise enclosed fixing rims for connecting with the metal frame and movable rims which are located in the blood channel, and wherein the movable rims of adjacent leaflets are joined to each other.

19. The surgical prosthetic heart valve of claim 18, wherein a sewing ring is fixed at the inflow side of the supporting structure, and the annular bands and the sewing ring are entirely covered by a first covering layer; and
   wherein the metal frame is entirely covered by a second covering layer, and the metal frame is abutted on the outflow side of the first annular band.

20. The surgical prosthetic heart valve of claim 1, wherein the deformable sections of at least one of the first annular band or the second annular band allow for expansion thereof while defining a maximum expansion diameter for the at least one of the first annular band or the second annular band.

\* \* \* \* \*